US008548828B1

(12) United States Patent
Longmire

(10) Patent No.: US 8,548,828 B1
(45) Date of Patent: Oct. 1, 2013

(54) METHOD, PROCESS AND SYSTEM FOR DISEASE MANAGEMENT USING MACHINE LEARNING PROCESS AND ELECTRONIC MEDIA

(75) Inventor: Michelle Longmire, Palo Alto, CA (US)

(73) Assignee: DermTap, Palo Alto, CA (US)

( * ) Notice: Subject to any disclaimer, the term of this patent is extended or adjusted under 35 U.S.C. 154(b) by 0 days.

(21) Appl. No.: 13/590,485

(22) Filed: Aug. 21, 2012

Related U.S. Application Data

(60) Provisional application No. 61/645,031, filed on May 9, 2012.

(51) Int. Cl.
*G06Q 50/00* (2012.01)

(52) U.S. Cl.
USPC ......... 705/3; 706/12; 706/45; 706/46; 706/47

(58) Field of Classification Search
USPC ................. 705/2–4; 706/12, 45–47
See application file for complete search history.

(56) References Cited

U.S. PATENT DOCUMENTS

| | | | | |
|---|---|---|---|---|
| 8,109,875 | B2* | 2/2012 | Gizewski | 600/306 |
| 2002/0016720 | A1* | 2/2002 | Poropatich et al. | 705/3 |
| 2008/0194968 | A1* | 8/2008 | Drugge | 600/473 |
| 2008/0275315 | A1* | 11/2008 | Oka et al. | 600/306 |
| 2009/0245603 | A1* | 10/2009 | Koruga et al. | 382/128 |
| 2010/0185064 | A1* | 7/2010 | Bandic et al. | 600/306 |
| 2011/0009707 | A1* | 1/2011 | Kaundinya et al. | 600/300 |
| 2011/0040571 | A1* | 2/2011 | Warren | 705/2 |
| 2011/0123076 | A1* | 5/2011 | Choi | 382/128 |
| 2011/0301441 | A1* | 12/2011 | Bandic et al. | 600/306 |

OTHER PUBLICATIONS

Liu, L., & Liu, J. (2011). Mobile phone-enabled control of medical care and handicapped assistance. Expert Review of Medical Devices, 8(6), 757-68. doi: http://dx.doi.org/10.1586/erd.11.32—best available proquest NPL search.*

* cited by examiner

*Primary Examiner* — Mark Holcomb
(74) *Attorney, Agent, or Firm* — Geeta Kadambi; Riddhi IP LLC

(57) ABSTRACT

There is a dire need to reduce healthcare costs and appointment times with specialists. The instant mobile device method, process and the system addresses this need. The system and mobile application allows the user/patient to interact with health care providers who are certified to work in a particular geographical region without hesitation. In the instant application a novel mobile technology powered by unique image analysis software based on machine learning process to evaluate the submitted images for diagnostic purposes. The ease of approaching a health care provider by using the mobile device and getting matched to the right healthcare provider is another feature of this mobile application. The ease of providing case history and images for diagnosis and treatment is also novel.

18 Claims, 11 Drawing Sheets

METHOD, PROCESS AND SYSTEM FOR DISEASE MANAGEMENT USING MACHINE LEARNING PROCESS AND ELECTRONIC MEDIA

CROSS REFERENCE TO RELATED APPLICATION

The instant application claims priority to U.S. Provisional Application 61/645,031 filed on 9 May 2012. The U.S. Provisional Application 61/645,031 is hereby incorporated by reference in its entireties for all of its teachings.

FIELD OF TECHNOLOGY

This disclosure relates generally to designing and using electronic technology to access and provide affordable, quick and pertinent health care. More specifically, this disclosure relates to store and forward as well as real-time telemedicine using mobile technology, machine learning for diagnosis and patient management, and data storage based on cloud based computing for an individual to get medical treatment for disease management from an expert healthcare provider in a timely and affordable manner

BACKGROUND

The traditional procedure to approach a treatment method is to contact your provider, make an appointment and then visit a healthcare provider. Depending on the availability of the calendar of the healthcare provider the appointments may be immediate or delayed. The delay in getting care may be the deciding factor between getting cured or to get terminally ill. It may also not be cost effective for the insurer and the individual who needs minor but frequent visits for minor problems. There is a need for affordable and accessible medical care solutions that leverage new technologies.

SUMMARY

Several methods, process and systems for disease management using mobile technologies and machine learning component and electronic medium comprising several machine-readable medium are disclosed. In one embodiment, a method for creating a mobile device based image acquisition, analysis of the submitted image for a disease condition using machine learning process, user and physician connecting using the disease management system for diagnosing and receiving treatment is described. In another embodiment, a process of enabling the user and physician to connect to get diagnosed and treated using a mobile device is described. In another embodiment, a system that may be manual, semi-automatic or automatic for the user to upload images of their disease condition, analyzing the submitted images using machine learning process and for the physician to diagnose and treat is described.

In one embodiment, a method for a user to become a member by logging in into the disease management program. After becoming a member the member is prompted to upload their medical background in one embodiment. In another embodiment, the medical history of the user is stored in a database with secure HIPAA compliant and encryption controlled set of rules. In another embodiment, the user is prompted to select an area of discomfort or where a medical attention is required. The user is then led through the system of a series of pertinent questions to gather the background information. This process may be automated, in one embodiment, by requesting the user to upload a preformatted medical history. Once the user has passed this step, in one embodiment, they are prompted to take pictures or write symptoms for the area of medical concern they are seeking. If the user is taking pictures they are prompted to take pictures using the device from a variety of distances, location, verifying signs and different angles, in one embodiment. After attaching the image, in one embodiment, the user may select a provider based on price, location, wait time, expertise and/or based on insurance provider list of approved healthcare providers. The case is then sent to the cloud database and may then be accessed by a healthcare provider. The user pays for the treatment rendered.

In one embodiment, a health care provider can access patient pool by registering to a consortium created by instant invention. In another embodiment, the registration of the users and providers are made using local authority rules and availability of the providers. In one embodiment, medication providers, retail pharmacists, health care providers such as physiotherapist, nurses and medical technicians may be referred at a cost effective rate. Prescription fills and refills may be ordered to the nearest or user choice providers instantly. In one embodiment, a physician, a health care service provider, a medication provider and/or allied service provider may log in to offer services to the user. In another embodiment, a physician, a member of the consortium, may login and have a case listed for them in the system. It may be a new case or a follow up case. In another embodiment, the physician may decide to either accept the case or reject the case. In another embodiment, the system notifies the patient/system of the status of the case. Once the case is submitted, an authentication process is performed to verify the image. In one embodiment, once the case is authenticated the system processes the image using machine learning algorithms and/or the physician performs differential diagnosis via prompts or self-input. Once the differential diagnosis is performed the physician in another embodiment may either select the treatment from prompts or self-input the treatment proposal. In one embedment the system may prompt the user about the physician completion of case. The invoice is generated by the physician and the user electronically pays the disease management system.

In one embodiment, a disease management system consists of several modules that enable a simple and efficient integration of communication, data gathering, service rendering, security, HIPAA/HITECH compliance and data storage functions. The disease management system uses several software modules that may be embedded either in hardware. Firmware or sold as a standalone software. The user registration module, user communication module, healthcare provider registration module and healthcare provider communication module use a processor to run efficiently in one embodiment. The user registration module, user communication module, healthcare provider registration module and healthcare provider communication module have several components of modules within their system and they are described in the detailed description section. In another embodiment, the various modules are interrelated for maximum efficiency.

In one aspect the process of disease management involves use of a mobile device. The user registers and inputs several answers for the questions as prompted by the mobile system. The user is also prompted to take a picture of the affected area and submit it to a secure cloud database that can be accessed by a health care provider for diagnosis and treatment. The health care provider may, in one embodiment, accept or reject the case and provide diagnosis and treatment upon acceptance. In one embodiment, the picture is processed for validation and authentication using an image processing algorithm that involves comparing the submitting images to images on the World Wide Web and/or algorithms that validate that multiple images submitted are from the same human body. The processes are to ensure that the images are authentic patient data and not fraudulent. The output of the machine processing enables the healthcare provider to verify the image for plagiarism. Once the authentication is performed the machine learning process also suggests diagnosis and treatment. Using the diagnosis rendered in the machine learning image processing, a treatment is suggested and the process relays the diagnosis and treatment in an automatically populated physician note. The physician may choose to accept the solution provided by the machine learning process or render a different diagnosis and treatment. Various other entities such as insurance provider, medical students and resident physicians in training, researchers and allied health care provider may also use the system and help manage the disease efficiently for the user.

Other aspects will be apparent from the following description, figures and the appended claims.

BRIEF DESCRIPTION OF DRAWINGS

Example embodiments are illustrated by way of example and no limitation in the tables and in the accompanying figures, like references indicate similar elements and in which.

Figure 1:
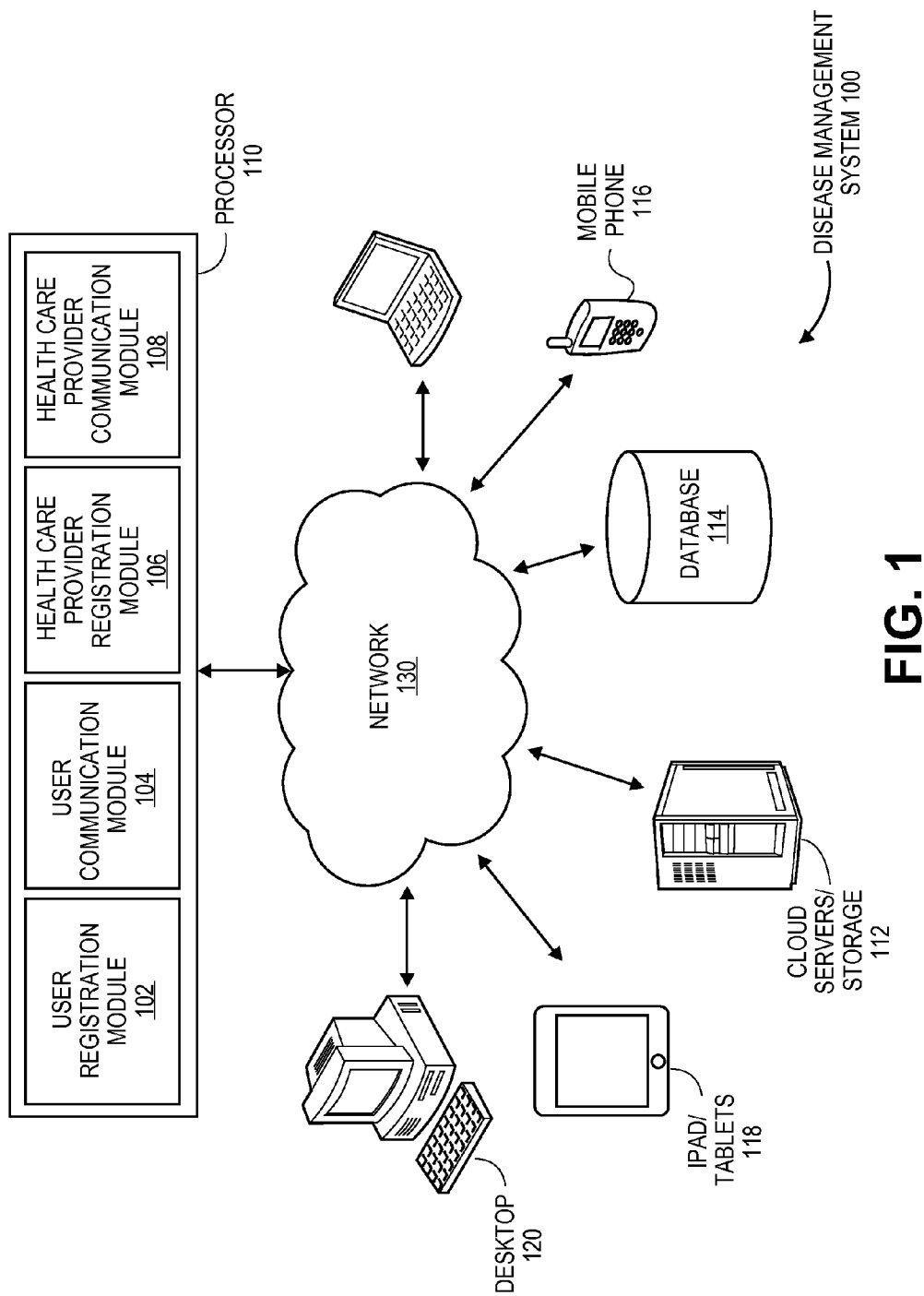
FIG. 1 shows an overview of the disease management system 100, in one embodiment.

Other features of the present embodiments will be apparent from the accompanying figures and from the detailed description that follows.

DETAILED DESCRIPTION

The instant disclosure describes a technological advancement for affordable and accessible health care. A method, process and system for disease management using mobile devices and machine learning process comprising image based diagnostic tool and electronic media is described.

In one embodiment, a practitioner may provide HIPAA complaint prescription, recommendation, diagnosis, advice, appointment, communication with health care provider (HCP) within the network; communicate with other HCP of the patient, message and live communication using video or any other means.

In one embodiment, an application that may be used on any mobile device such as tablets, cell phones, and mobile computers. In another embodiment, a method of matching medical practitioner based on the inquiry by the user created on a mobile device is done. The match may be based on expertise, practice techniques, proximity, availability, membership and local authority rules. Local authority rule is something all licensed practitioners have to follow and may not be able to provide services outside of their area. There may also be an option for the non authorized practitioners to provide recommendations to the complaint practitioners that they are aware of.

In one embodiment, if the user or individual is a member of the network for the mobile application then they may be able to access the database that stores medical history of the particular user. The user may also populate their medical history for the care takers such as doctors, nurses and other medical related personal to use. The database is cloud based database and will be dynamically updated. The entire system and service is security enabled and password protected so that it not only complies with regular security rules but also HIPAA compliance and patient privacy rules. The whole system is also HITECH compliant for audit review if need be.

The instant mobile application's method and system may be supported by financial payment software so that the providers, care givers, prescription providers and pre and post care providers are paid either by the user directly using the system or the insurance company. The patients may opt to deposit a certain amount in this system so that they don't have to provide financial information every time they use or in an emergency situation. The system may rely on credit card image recognition technologies to obtain payment information. The user will have the opportunity to pay directly for the service rendered without insurance usage. The payment may be divided on a subscription basis. This is specifically useful because more and more users are hesitant to use their insurance to pay for less serious or preliminary care or during travel unable to reach their primary practitioner malpractice issues.

In one embodiment, health care providers such as PPO or hospitals can reduce the less serious patient appointment and reduce insurance payment burden by providing this mobile device service to their members. This would reduce the burgeoning health care insurance cost to the government and the user. Physicians may be able to devote their time to more serious patients and provide better care. The paper work is also reduced and time is saved by automating the user and the healthcare provider (HCP) interaction using machine learning the data is automatically captured and stored in the cloud. The data may in the form of text, automated forms, and photo, video or audio files. Physician should be able to share their cases with other physicians and get expert opinions, consult or transfer cases. The disease management technology that comprises of mobile application technology and cloud based data storage and retrieval may also be embedded into social media web sites, individuals web pages, mobile devices, insurance company web sites, any group that covers medical insurance, hospitals, and pharmaceutical companies.

In one embodiment, a method of using the mobile application is described. The user becomes the member of the consortium. The disease management consortium comprises of health care provider (HCP), user (patient), insurance company and other healthcare providers such as drug companies. The name disease management consortium is being used to represent a group of medical care provider and receiver personal. Once the user is approved for membership based on certain criteria they are requested to provide their health profile. Once they provide their personal medical information it is stored in the cloud based secured database. The user has an active application on their mobile device to access diagnosis and treatment by the member HCP. Costs are low and transparent because there is little overhead cost (no physical building space, etc). The HCP becomes a member either through their associations, local authority associations, hospital or private practice group or individual. The may pay a membership fees as well to be a member of disease management consortium. The HCP may be divided into specialties such as dermatologist, immunologist and family practitioners. They are not limited only these specialties but as an example we propose these. Once the membership is established then the system makes sure it is HIPAA compliant. It may even prompt users and HCP to not communicate certain forms of communications if it thinks it is not secure or HIPAA complaint.

Once the mobile application is downloaded to the user mobile device the user may be registered before or at that time or in the near future can access the HCP. If the user is accessing without becoming a member a short questionnaire can register them temporarily and then subsequently they be requested to get membership level information. The user may tap on the application, fill out their symptoms, upload image and request for a specific doctor or a HCP or just let the Disease management consortium suggest the best match. The Disease management consortium may also have fixed rate access to HCP for a particular service.

In one embodiment, the HCP connects to the cloud database of patient cases. An HCP can review a case without any private health information simply to evaluate adequacy of image quality. The HCP can deny or accept a case based on image quality or appropriateness of the possible diagnosis for telemedicine. If the image is not of adequate image quality to render a diagnosis, the HCP can notify the patient that the images need to be revised. If the HCP identifies an emergent condition the provider can send the user a message through the application as well as send a text message or phone call alert that the user needs emergent medical attention. If the HCP deems the images of adequate quality he/she accepts the case and at this point detailed patient information is relayed to the HCP. The HCP may request the user to provide more information, video chat or talk to the patient to get a full case history. The HCP may provide prescriptions and send them via electronic data transfer to the pharmacy that is closest to the user and/or to the pharmacy selected by the user. The pharmacy may also become the member of the consortium. The HCP may provide other means for getting prescriptions filled if the pharmacy is not a member. This system reduces unnecessary office visits and frees up time and cost for more serious medical issues. All this communication and transaction is stored in the cloud and HCP or the user is review the history as a medical record. In one embodiment, to further reduce the time to be spent by the HCP and communicate effectively the treatment options may be radio buttoned so that the HCP.

In another embodiment, the scheduler in the disease management system also may use the GPS location of the cell phone to match the user with a HCP in the area, to match the user with a pharmacy, or to recommend a HCP in the area. The user may input standard medical records information to the HCP so that they can make an informed decision based on prior medical history. All these inputs may be made easy by providing drop menus or radio buttons.

FIG. 1 shows an overview of the disease management system 100, in one embodiment. A user in this application may comprise of individuals, patients, parents and any patient-approved assistant for a patient. In one embodiment, a user can access the provider using a mobile device application and access medical care. The electronic media may comprise of mobile devices, computers 120, tablets 118, mobile phones 116, e-readers 124, cloud servers 112 and database 114 for storage etc. All the components are connected with each other using a network 130. A processor 110 comprising of several modules houses user registration module 102, user communication module 104, healthcare provider registration module 106 and health care provider communication module 108. Cloud based server or storage device 112 enables the disease management system 100 to be accessible and unified for ease of management and accessibility from anywhere in the world.

Figure 2:
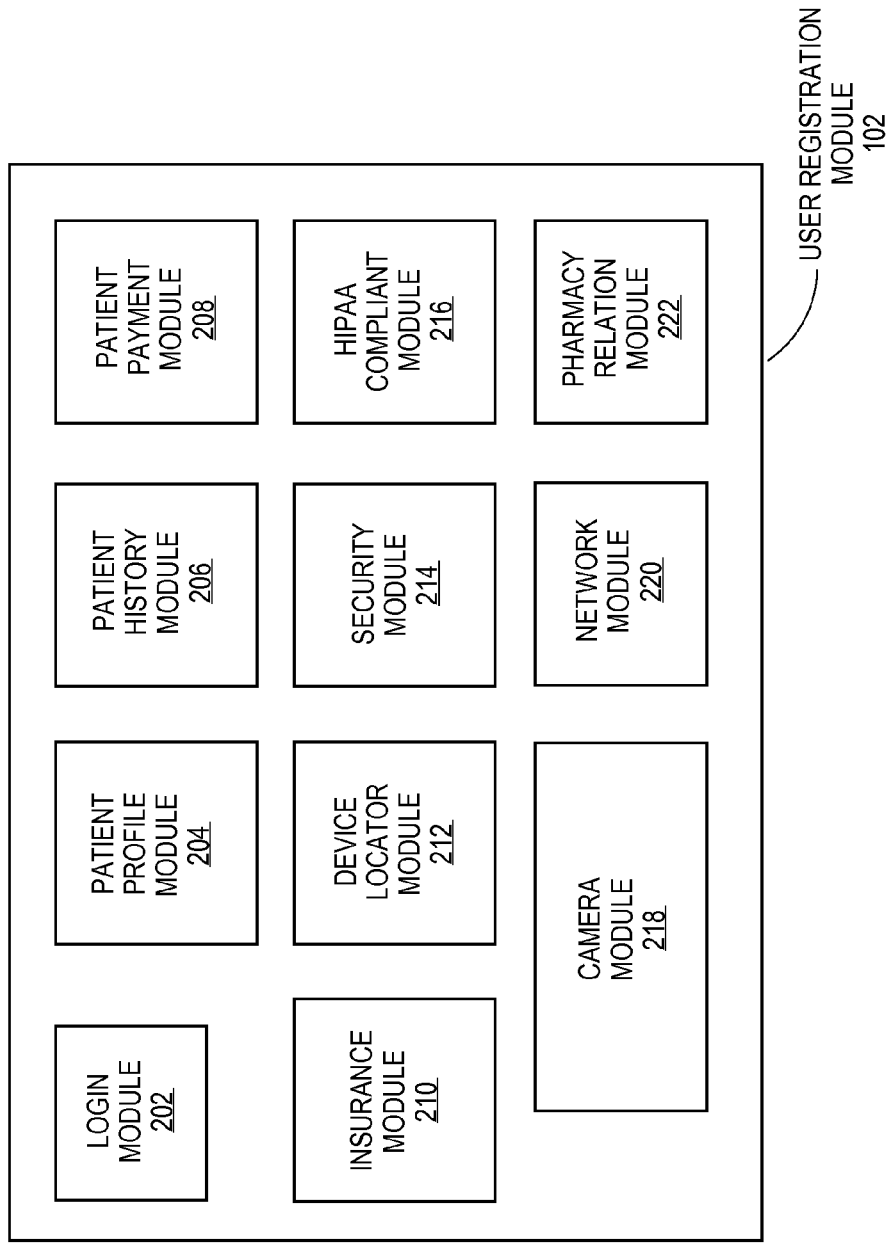
FIG. 2 shows a detailed user registration module 102.

FIG. 2. is an expanded view of the user registration module 102. A login module 202 enables the user to login. There are several levels of authentication that may be implemented to verify the login values. Patient profile module 204 enables the user to input their profile which may comprise of location, treatment preference such as onsite or mobile application based. Patient profile module may also collect general demographic information about age, gender. Patient history module 206 may be designed as a self-reported medical history page to enter current and past medical conditions, current and past medications, surgical history, family history of disease, with area to enter in user language, provide prompts, or a combination of both. It may emulate basic hospital forms so that it may be stored in databases easily. HIPAA compliant software is essential to protect information security risks and penalties associated with HIPAA/HITECH. HIPAA compliant module 216 has to take into consideration of HIPAA rules. For example: ensure that the display image has a 30-second to 2 minute time-out feature. The user should be trained by a video for complying to protect their data and educated about the password protection during login process. Security module 214 helps the HIPAA compliant module 216 and the network module 220 to be secure as well as HITECH/HIPAA compliant. It may also help as an audit module for insurance audits later down the road. Patient payment module 208 enables the user to pay using personal credit cards, debit cards or prepaid insurance cards to the vendors such as pharmacy, physical therapist etc., or the HCP for their consult. Payment module 210 allows the users that are members to approach available HCPs through their list for the user to approach the physicians for consult, pays them through this module or pays the service that was rendered to the user. The camera module 218 allows user to take pictures of their ailments, affliction on their body, take an image of somebody else with physical visible disease condition and send it for diagnosis and treatment. The camera module also allows the user to video record their infliction for the physician to see and use that for diagnosis and treatment. The mobile camera can be used to take images that are then saved to the secure cloud database in a "Store and Forward" method. The mobile device camera may also be used to create a video that is saved to the secure to the cloud database in Store and Forward method. The mobile device camera can also be used for real-time video conferencing with the HCP. The final scenario is a combination of both Store and Forward and a real-time video conferencing for a hybrid model. All methods of image and video acquisition may involve a guided process whereby the user is guided through a step-by-step process to obtain images and videos with pertinent and high quality information. In the Store and Forward image and video method the user is guided through these steps 1) close up focused image, 2) farther image that depicts the body part that is affected, 3) image that involves a fixed anatomic landmark in relationship with the skin condition and 4) photos of other similar appearing lesions (ie, other moles but not the one of concern or other areas of the rash, for comparison.

Figure 3:
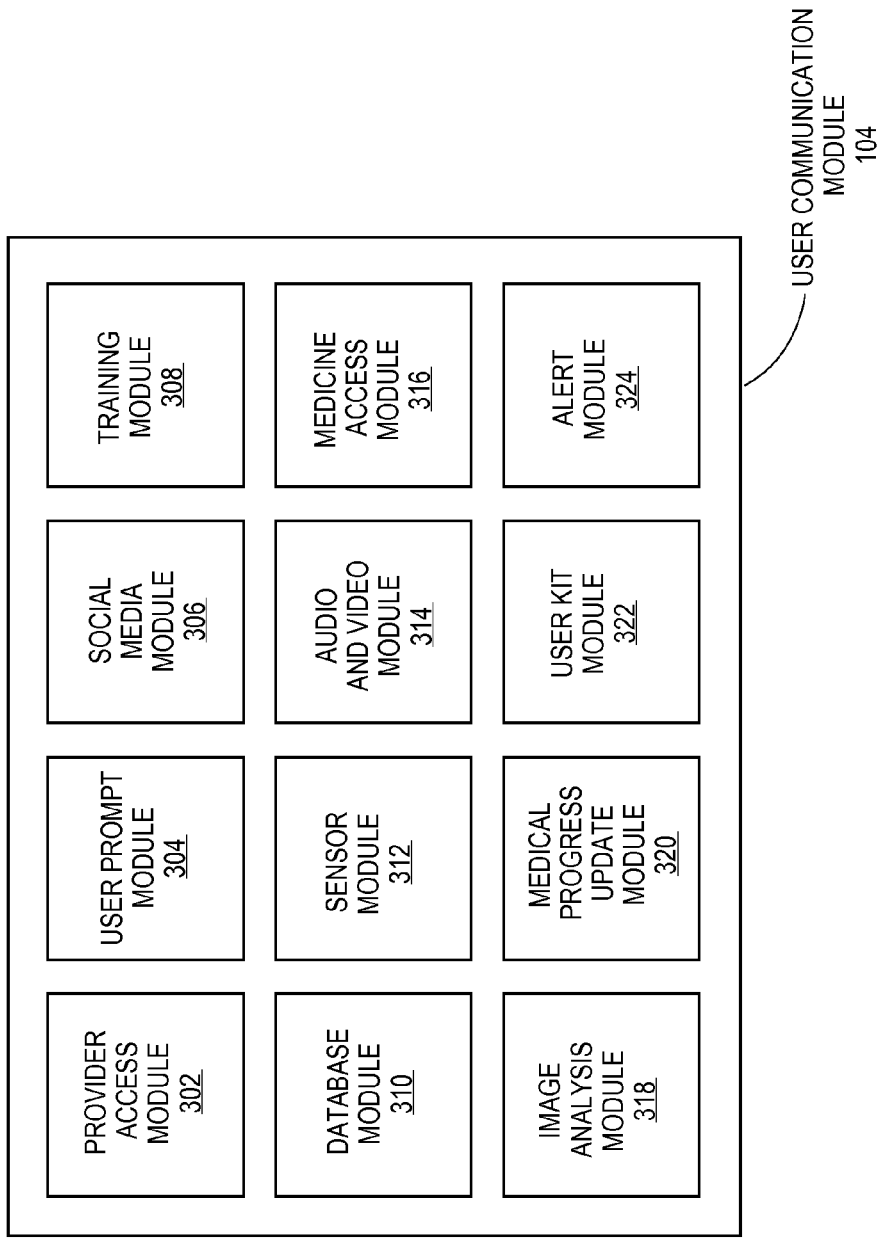
FIG. 3 shows a detailed user communication module 104.

FIG. 3 shows the detail version of user communication module 104. Provider access module 302 is a method for provider such as physician, pharmacies, and other allied health care providers such as physiotherapist, nurses, and home care providers etc., to connect with the user. Based on the user preference, security clearance, HIPAA compliance and credit checks a provider may be able to approach the user for services and selling goods. User prompt module 304 is a means for reminding the user to take medication. The user prompt module may also allow the designer of the software to create user prompts for filling the forms, medical history profile and pharmacy requests etc. automatically or by providing choices. Social media module 306 enables the user to access various social media sites to connect with other members or friends or blogs or feeds for suggestion, feedback on physician services, suggestions, provider services etc. Training module 308 allows the user to be trained either using video, set of instructions in script format or combination of both. The right way of using the disease diagnosis method is critical to get proper diagnosis and treatment. The user may be prompted to take proper images, if the image quality is not good requested to retake, fill all the sections in the medical history form, symptoms, and other pertinent information regarding their ailment. Database module 310 not only allows the system to be backed up with user data but also complies with HIPAA/HITECH rules for data mining and sharing. Cloud based storage is being implemented for this mobile device based instant invention. Sensor module 312 allows the system and the user to use temperature recordings, quality of image check gauge, picture correction capability for the camera module and other sensor based technology for gathering, conveying and recording data for diagnosis and treatment. Audio and Video module 314 allows the user to communicate with several modules such as training module, physician contact, uploading the video and audio of their ailments etc. All these modules are producing data and each data is stored and secured using the database module. Medicine access module 316 will allow the user to ask for price quotes from the health care service provider and get the best value for their money. The choices may also depend on accessibility, urgency and mode of delivery of the medicine. Medical progress update module 320 allows the user to get communication from the physician and/or provider about their progress based on diagnostic tests. User kit module 322 includes measurement tools such as height, weight, temperature, blood pressure and physical tool to help with disease evaluation and management. Alert module 324 may aid reminding the user for a particular task such as medication consumption time, or a physician response or a pharmacy fill status etc. The instant modular disease management system and method enables a comprehensive user care for diagnosis and treatment for a particular disease such as acne. More examples will be discussed later as examples.

Image and data analysis module 318 used in the user communication module has a critical function to not only capture the image but also for further processing of the image and associated data for diagnosis and treatment. Image and data analysis using machine learning for automating diagnosis and treatment and computer vision-facilitated diagnosis and treatment is central to the claim. This includes image analysis for 1) image authentication 2) machine learning 3) data mining for knowledge discovery, 4) computer vision. The machine learning component may be used to diagnose and/or to develop algorithms for assisting HCP in diagnosis and disease management and treatment. The component may also include assisting HCPs to understand HPC errors and reduce medical errors. The machine learning component will rely on creating algorithms using a) unknown properties within images as well as machine learning from b) labeled images. For example the process will involve presenting the system with an image without any information as well as presenting the system images with a known diagnosis. Images used to create machine learning algorithms will be a) acquired from user submitted images and/or b) open source image databases such as the national library of medicine c) and/or electronic textbooks. Using these image datasets machine learning algorithms will be adapted to automatically learn to complex patterns within the images. Machine learning algorithms include but are not limited to a) supervised learning whereby our experts are labeling images with diagnoses and using these for learning, b) unsupervised learning whereby unlabelled images are presented and the system discovers previously unknown or untold patterns in the images, c) semi-supervised learning that combines both labeled and unlabeled examples to generate an appropriate classifier, and d) transduction methods to predict new outputs on specific and fixed cases from training cases. The machine learning program will then be used to process previously unseen images in order to render a single diagnosis or multiple possible diagnoses. This will increase physician efficiency so that many more patients can be cared for in a safe and timely manner. These diagnoses will then be used to automatically generate treatment recommendations that can be communicated the HCP or user. Methods include 1) decision tree learning, 2) association rule learning to discover interesting relations between variables, such as number of cases seen and HCP errors in diagnosis or treatment, 3) artificial neural networks in which computations are structured in terons of interconnected group of artificial neurons in order to model complex relationships between inputs and outputs to find patterns in data or to capture the statistical structure in an unknown joint probability distribution between observed variables, 4) genetic programming evolutionary algorithm-based method to optimize a population of computer programs according to a fitness landscape determined by a program's ability to perform the given task, in this case for example to make an accurate diagnosis from an image or identify physician error, 5) inductive logic programming, herein given an encoding of the known background knowledge and a set of examples represented by logical database facts, the method will derive a hypothesized logic program, 6) support vector machines in which a set of related supervised learning methods are used for classification and regression and using the training examples, the algorithm builds a model that predicts whether the new example falls into one category or the other, 7) clustering as a method of unsupervised learning for uses such as but not limited to statistical data analysis, 8) Bayesian networks as a probabilistic graphical model to represent a set of random variables and their conditional interdependencies via a directed acyclic graph, for example to represent probabilistic relationships between diseases and symptoms. For example, given symptoms the network can be used to compute the probabilities of the presence of various diseases. 9) Reinforcement learning to understand how an HCP ought to act in an environment as to maximize long-term gain and positive outcome. 10) Representation learning using mostly unsupervised learning algorithms to discover better representations of the inputs provided during training. 11) Sparse dictionary learning to determine which classes a previously unseen datum belongs to for the purpose of but not limited to disease type identification and image denoising. One broad example of machine learning for computer vision is the input of labeled images that the HCPs have diagnosed or labeled images from electronic textbooks as inputs to develop algorithms that can be applied to unlabeled images with outputs being diagnosis and treatment recommendations, even in the form of a filled-out physicians note including diagnosis with an associated billing code, such as an ICD-9 code, and specific treatment.

Figure 4:
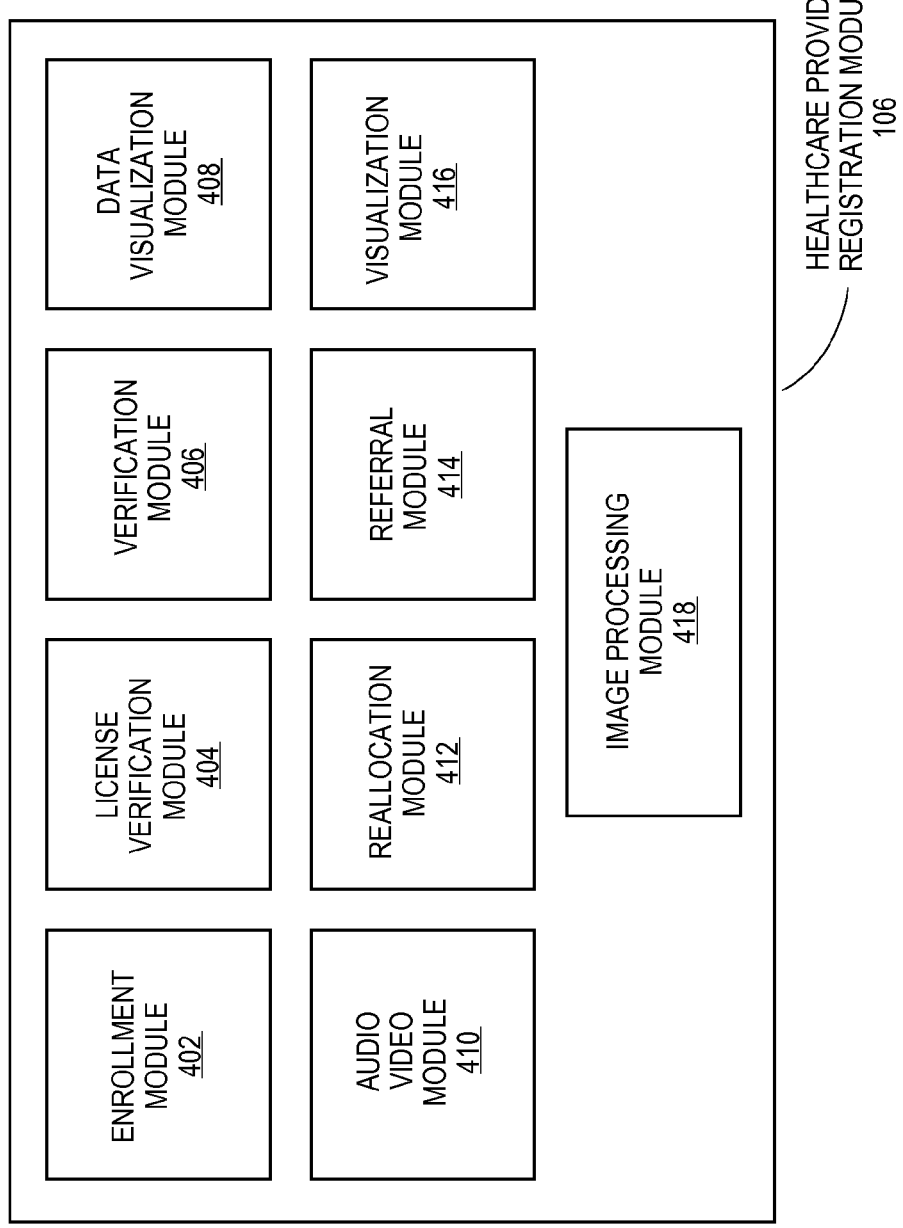
FIG. 4 shows a detailed healthcare provider registration module 106.

FIG. 4. Is the healthcare provider registration module 106. It enables the provider such as physicians, pharmacists, nurses, physiotherapist, diet and medicine providers and other allied health professional to form a consortium or membership to a particular user. The enrollment module 402 allows the providers to register and comply with the same HIPAA/HITECH rules so that patient confidentially is never compromised.

In one embodiment, a health care provider can access patient pool by registering to a consortium created by instant invention. In another embodiment, the registration of the users and providers are made using local authority rules and availability of the providers. In another embodiment, medication providers, retail pharmacists, health care providers such as physiotherapist, nurses and medical technicians may be referred at a cost effective rate. Prescription fills and refills may be ordered to the nearest or user choice providers instantly. Insurers may save money by belonging to the consortium.

License verification module 404 would verify the status of medical license for professionals such as physicians and nurses to ensure that all members of the consortium had active licenses and are eligible for medical practice. The license verification system may be specific to the country of origin and the module would follow the local authority rules and comply with their requirements. The license verification module may also flag the cancelled license and remove them from the consortium. Verification module 406 has multivariate functions including verifying board certification, licensure in various states, up-to-date medical credentialing, and/or contacting professional references.

Data visualization and HCP image interaction module 408 allows the provider and the user to preview the image, expand on the image and rotate the image for clarity and observation for diagnosing. Many platforms may be used to display the image for any given operating system. The disease management system may recognize the optimal program suitable for a device of use. Such as android application may be compatible to certain display software and the disease management system may suggest the user and the provider to use the optimal display program or mode. This is just an example and many other platforms that are currently being used will be used for implementation. The HCP may use touch-screen interaction to virtually draw or highlight on the image for the purpose of demonstrating to the user where to apply treatments. Treatments include but are not limited to topical creams both prescription and non-prescription. These treatments may be depicted in the same image with different colors so that the user can easily see how to use the recommended treatment. For example, an HCP visualizes images of acne submitted by a user. The HCP uses touch screen virtual drawing to draw on the submitted image a blue virtual paint in the areas that the HCP wants the patient to use topical treatment A. The HCP then virtually draws on the same image with a green virtual paint to depict the anatomic location or region for application of topical treatment B. The HCP may use touch screen interactions to virtually draw or highlight an object in an image for the purpose of pointing the object out to the user. For example, the HCP may draw on circle using touch-screen virtual drawing.

Audio video module 410 allows the physician to see and hear if the user has recorded their input along with the image. They can also record and capture their voice for the user. The physician may also record their instructions and treatment mode and suggest other options to the user. Reallocation module 412 is unique module in this invention and provides opportunity for the physicians to allocate the case to another physician who may be an expert in the field or has more time to work on the case. The physician may decide to reallocate the pharmacy or any allied health field help depending on pricing scale preference by the user or geographical preference by the user. The referral module 414 may allow one specialty physician to refer another specialty physician for the user. This may sound as if it is just introducing one physician to another but the instant disease management system is HIPAA and HITECH compliant to share records, share images and differential diagnosis notes with the system certified user, physicians and other healthcare providers. Image analysis module 418 may perform the functions of image analysis, verification, authentication and storing images for diagnostic, treatment and future use.

Figure 5:
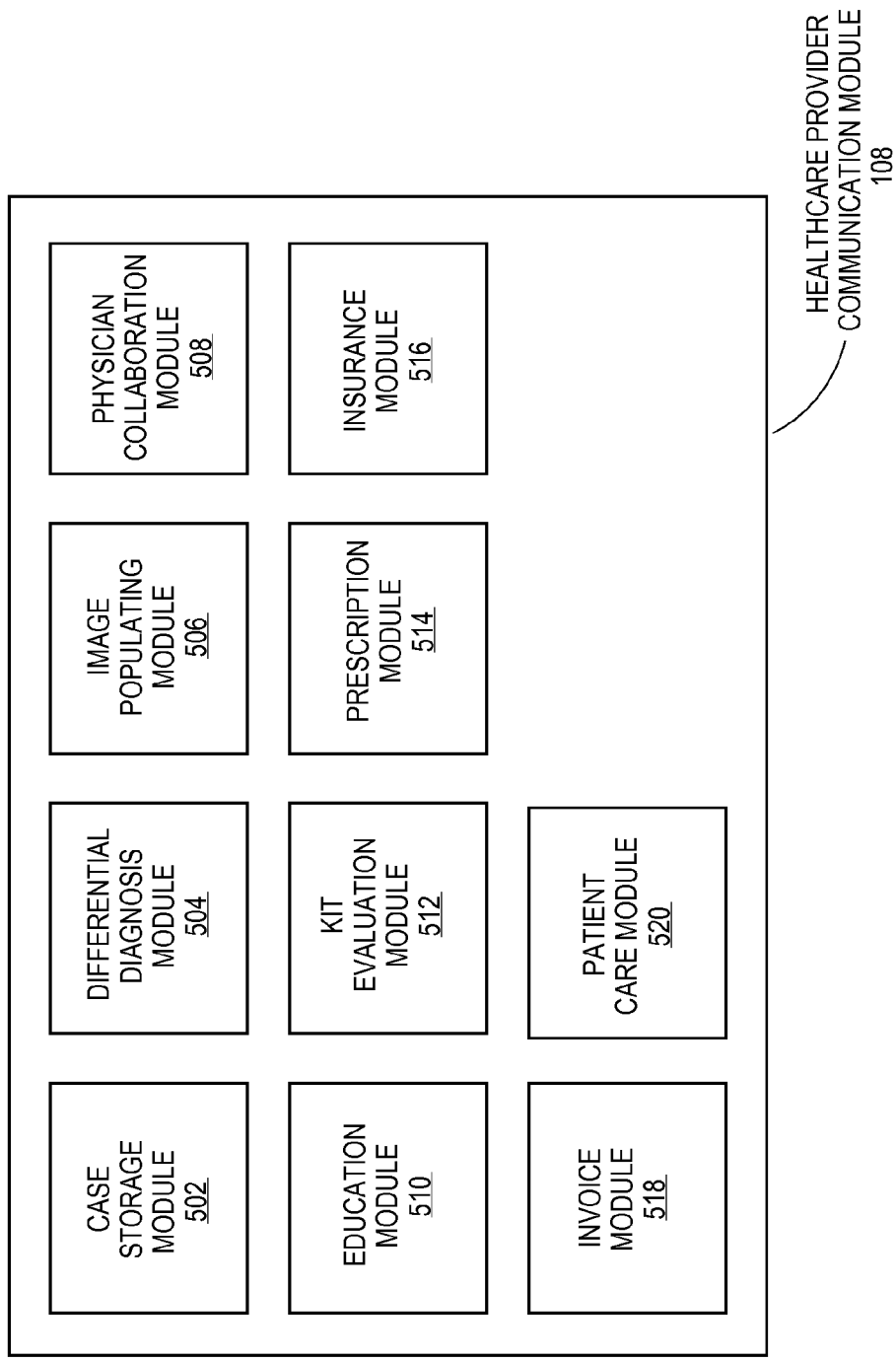
FIG. 5 shows a detailed healthcare provider communication module 108.

FIG. 5 shows an expanded healthcare provider communication module 108 that comprises of Case storage module 502, Differential diagnosis module 504, Image populating module 506, Education module 510, Kit evaluation module 512, Prescription module 514, Insurance module 516, invoice module 518 and Patient care module 520. Case storage module 502 is a novel approach to aid physicians in training, image analysis to use the images for machine learning analysis, cloud based HIPAA compliant database storage opportunity for the physicians that have created a repository of cases during their practicing career. This module may be searchable based on patient/case demographics, diagnosis, age of patient and date of treatment etc. These are just examples and the list is not limited to these examples.

Figure 6:
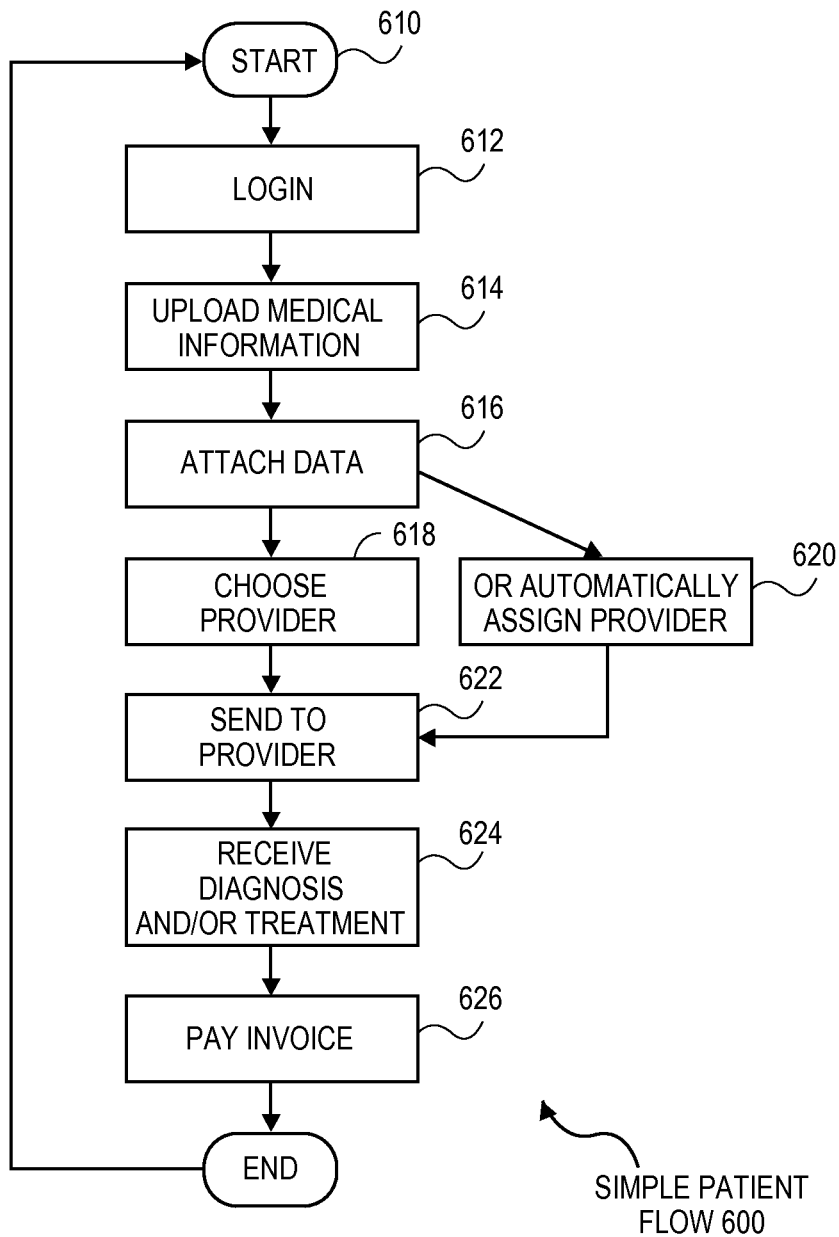
FIG. 6 shows a flow chart of a simple patient flow 600.

FIG. 6 shows a typical flow for a user. A user may tap on the mobile device icon for disease management software use to start the program 610. A registering/login 612 functions by a user to use the data management system to obtain a treatment for a disease using an electronic mobile machine is the first step in the simple patient flow 600. Once the user or patient has logged in they may upload a user medical history 614 to enable complete the registration by at least one of a self-filling form and prompt by offering predefined question and answer. The user may also attach their data 616 for further processing. The image processing module 418 may accept or reject the image taken by a camera after quality checks and permit the user to upload an image of a particular region of a user body. The uploaded image is authenticated by verifying from the database if it is a stock image or real image of the body of the person. The verification if it is the same as the body of the person may be performed by asking the user/patient to take images from various regions and compare the skin architecture with stored and other images. The images from different triplicates as first image, second image and third image are converged to not only enhance the image quality but also to authenticate and verify the images. This step is important to reduce abuse of the system to gain inappropriate diagnosis and treatment. Also it prevents non registered members to take advantage of another members registered account. As this system may be set up in such a way that only one person may use it for a particular registration name and number. The user may elect to choose 618 their own provider, such as physician and/or pharmacist. The disease management system may also select and assign providers automatically 620. Once a provider has been elected or selected by the system the health data is sent to the provider 622. The user waits for the diagnosis and treatment from the physician and they are informed once it is received 624 by the disease management system. The user then pays the invoice 626. The diagnosis and treatment is performed by recognizing a pattern using a machine learning software running on machine readable medium and comparing the control image data to a centrally stored database created by a consortium of national level such as DermAtlas, National Library of Medicine, as well as images in electronic textbooks, and images submitted from users or HCPs in the system and physician self-created images. Storing the data generated by the user, medical history, forms, the image of the particular part of the body and the pattern for differential diagnosis in at least one of a local database and cloud server is essential and is performed on a routine basis.

Figure 7:
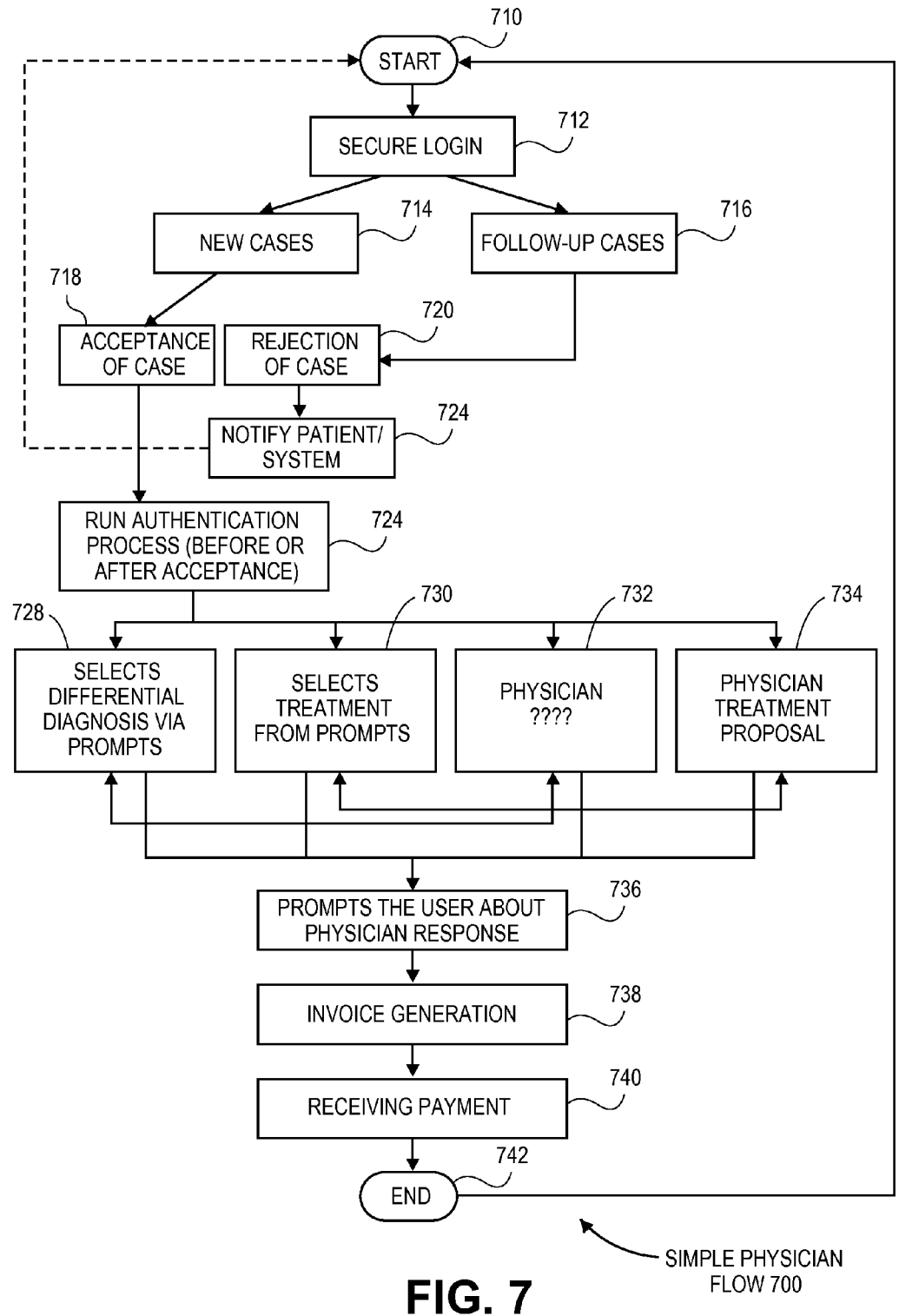
FIG. 7 shows a flow chart for a simple physician flow 700.

FIG. 7 shows a simple physician use flow 700. It may be modified and made complex. In the following paragraphs many additional functions by the system and methods are illustrated. The physician also registers. Authentication of their medical license is done using license verification module. Once the physician registration is accepted one may permit the physician to access the data generated by the user to provide a differential diagnosis. These are all secure login 712. The physician may decide to view new cases 714 or follow up cases 716. The physician may decide to accept the case 718 based on the time constraint, complexity, expertise level and area and/or based on the sliding scale payment choice made by the patient. If one physician rejects the case 720. The user/patient is notified of the physician's action. If the physician does not take a case then the system automatically selects the next available physician based on the user selection criteria. If the physicians accept the case then the physician runs a authentication process f24 of the submitted image just to make sure it is authentic. The physician then views the provisional diagnosis data for the differential diagnosis proposed by disease management system and selects the diagnosis using prompts 728 and also treatment from the prompts 730. The physician has the role to overrule the prompts diagnosis and render his own diagnosis 732 and the treatment 734. Using the machine learning algorithms, the disease management system presents the HCP with several possible diagnoses or just one diagnosis. The physician then taps the diagnosis and the disease management system creates a note that has the diagnosis rendered in a relevant billing code such as an ICD-9 code as well as treatment suggestion. The physician can simply tap accept and the note is sent to the patient and the recommended prescription is electronically sent to the pharmacy selected by the patient and over the counter meds are automatically ordered from a distributor. The physician may render a diagnosis using at least one of the provisional diagnosis data, a physician diagnosis and a combination thereof; and prescribe a treatment to the user based on the diagnosis. The system then prompts the user about receiving an alert regarding the physician's rendering of the treatment 736. Either the physician's office generates the invoice or the system automatically generates the invoice 738 or the physician to be paid by the user. The physician receives payment 740 and chooses to treat another patient. The user obtains at least one of a treatment method, a medication, a consultation date, a referral to another service provider and a combination thereof from the physician. The physician may choose to demonstrate the use of the medication or application of the medication using audio/video module. The physician may demonstrate using touch screen technologies to draw on a topical treatment to the affected area or three dimensional technologies using hand gestures or augmented reality software to use virtual figures to show how to apply a cream for a skin condition in three dimension.

Figure 8:
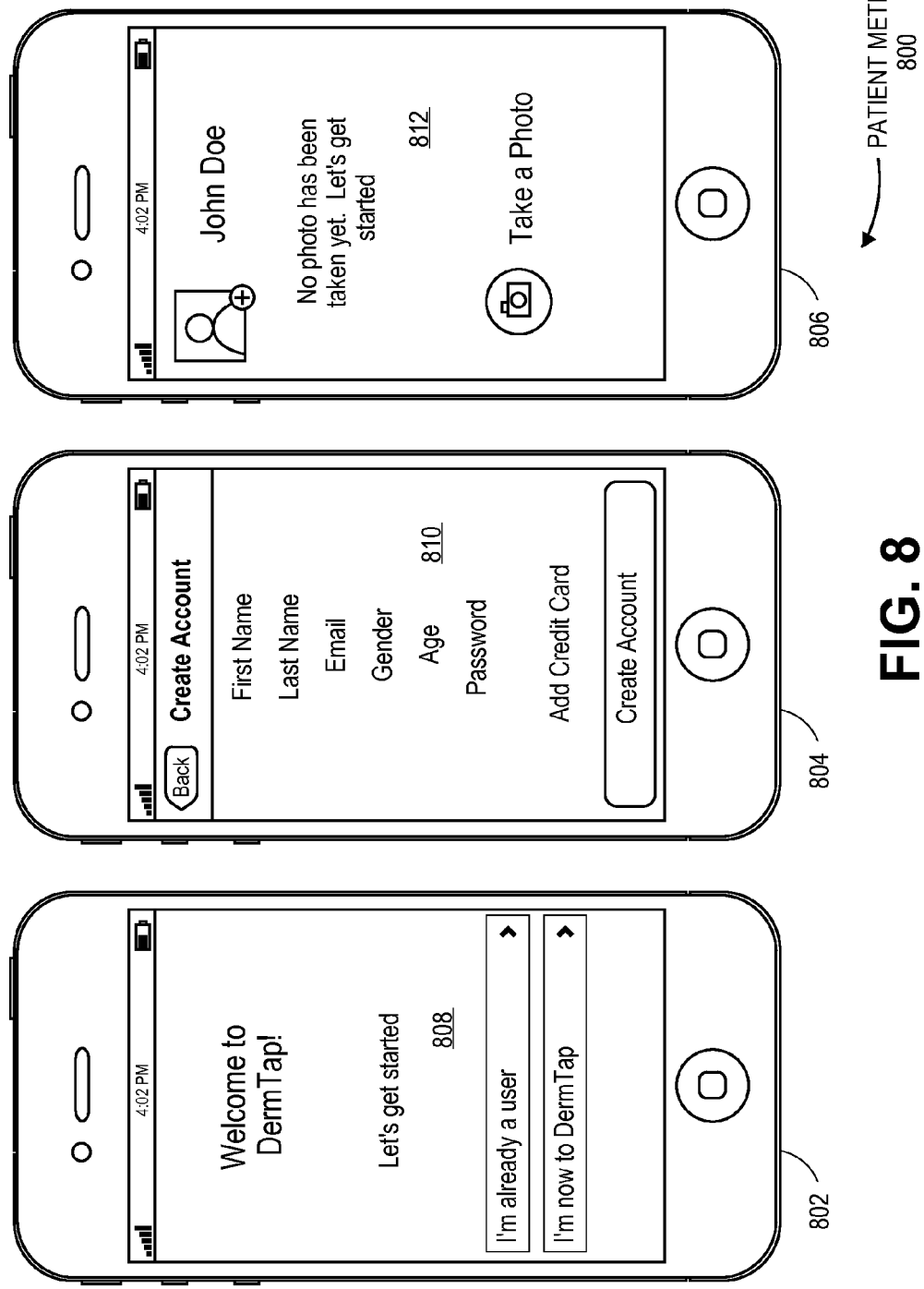
FIG. 8 shows a patient method 800 in a mobile device, in one embodiment.
Figure 9A:
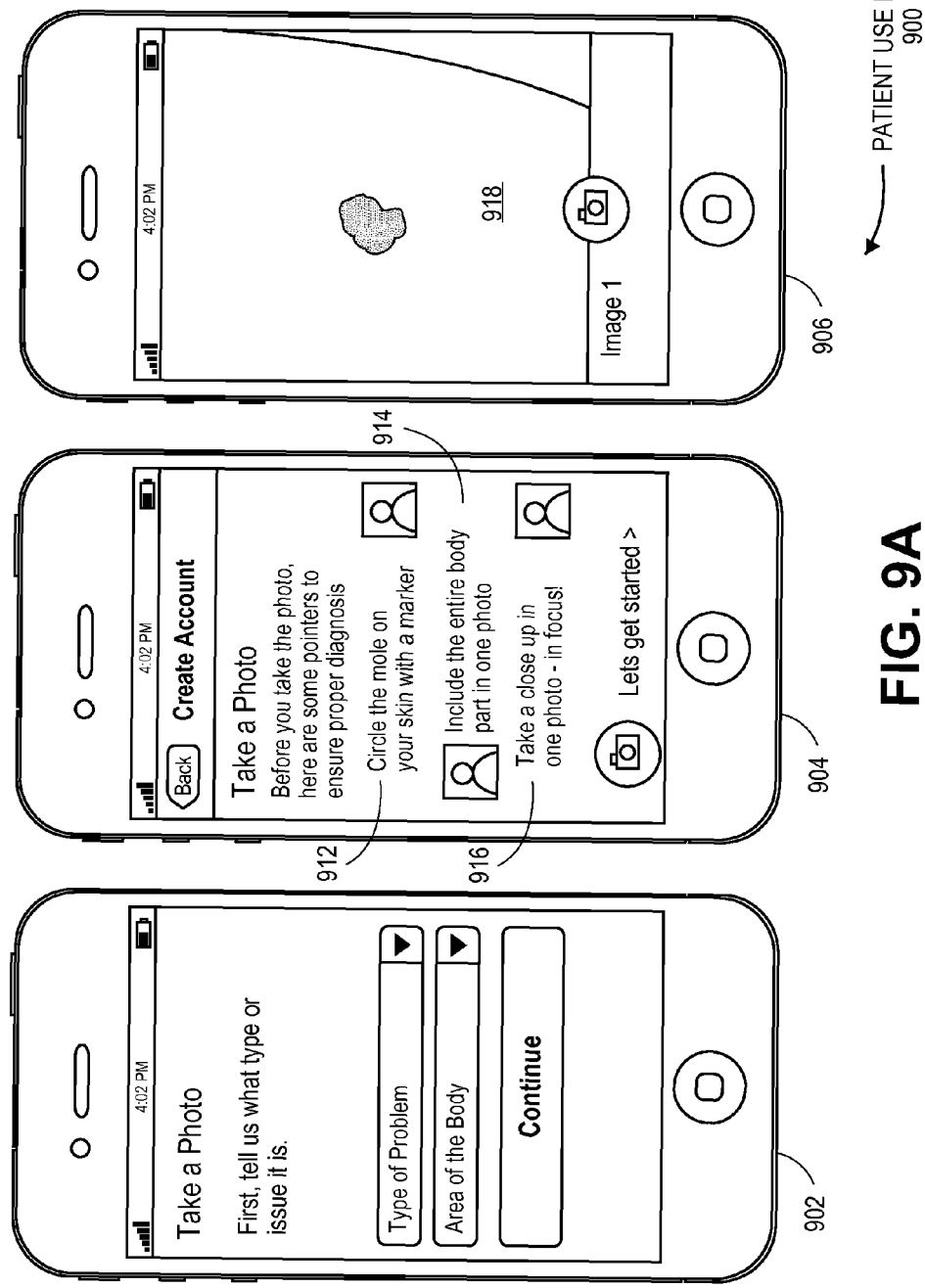
FIG. 9A shows the patient use process 900 in the mobile device.
Figure 9B:
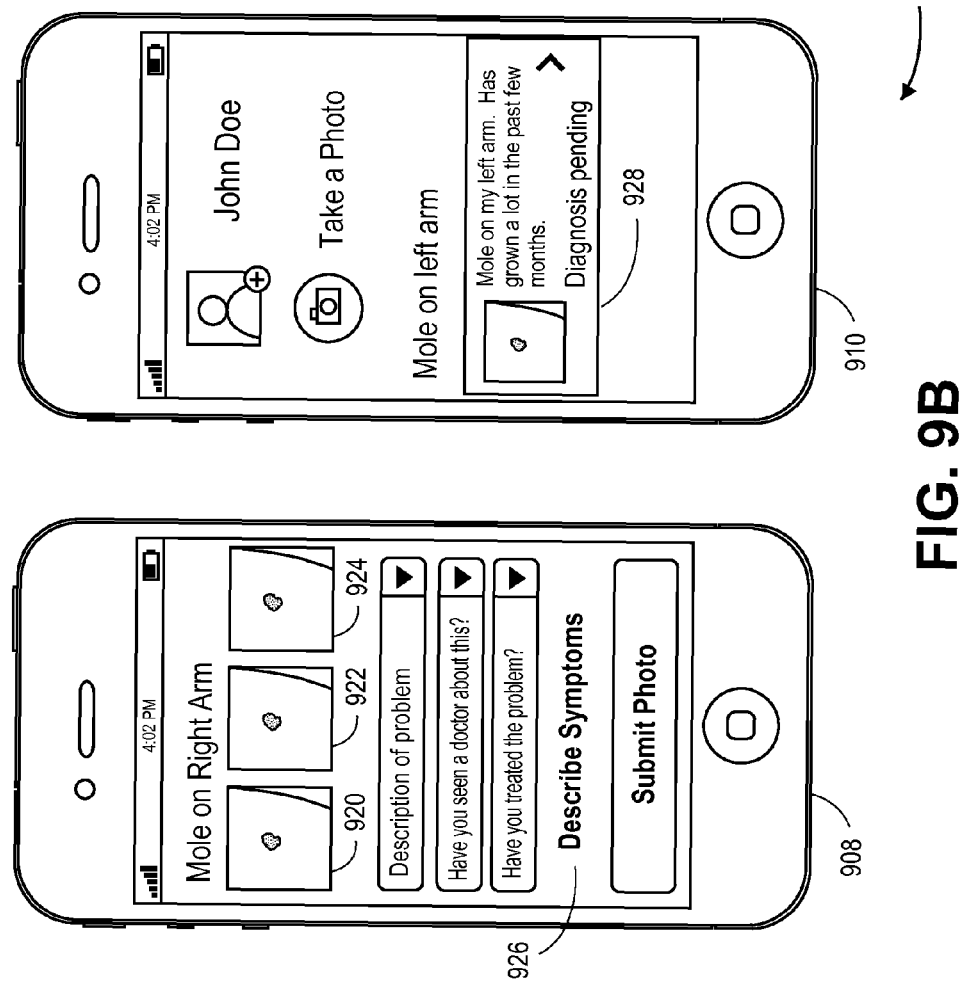
FIG. 9B shows another patient use process 900 in the mobile device.

FIGS. 8, 9A and 9B show a patient method and use process scenarios. The example is a mole in the arm. A mobile device in FIG. 8 is shown to have three screens for the user to get started. The first screen shot 802 shows an application welcoming the user to a software disease management system called DermTap™. The screen depicts that all of it just a tap away. Once the user taps on getting started they are prompted to create an account 804 or register. Regular parameters or fields such as first name, last name, email, gender, age, password and a credit card information is requested to be filled 810. Screen 806 prompts the registered user to take a picture to capture an image of the condition for the physician to evaluate. FIG. 9A shows the next three steps as figures. Step 902 walks the user through the types of problems so that at the backend it can be related to the right physician, pharmacist and all the folks those are associated with the consortium. 904 show how a user is prompted to take the image or photo of the afflicted area. First image 920, second image 922 and third image 924 is recorded. Once the image is captured in 906 the user can visually inspect. FIG. 9B shows in 908 prompts the user for some other drop down menus that may help the physician and describe the symptoms in user language in 926. Step 910 encourages for submission and shows the diagnosis pending status.

Figure 10:
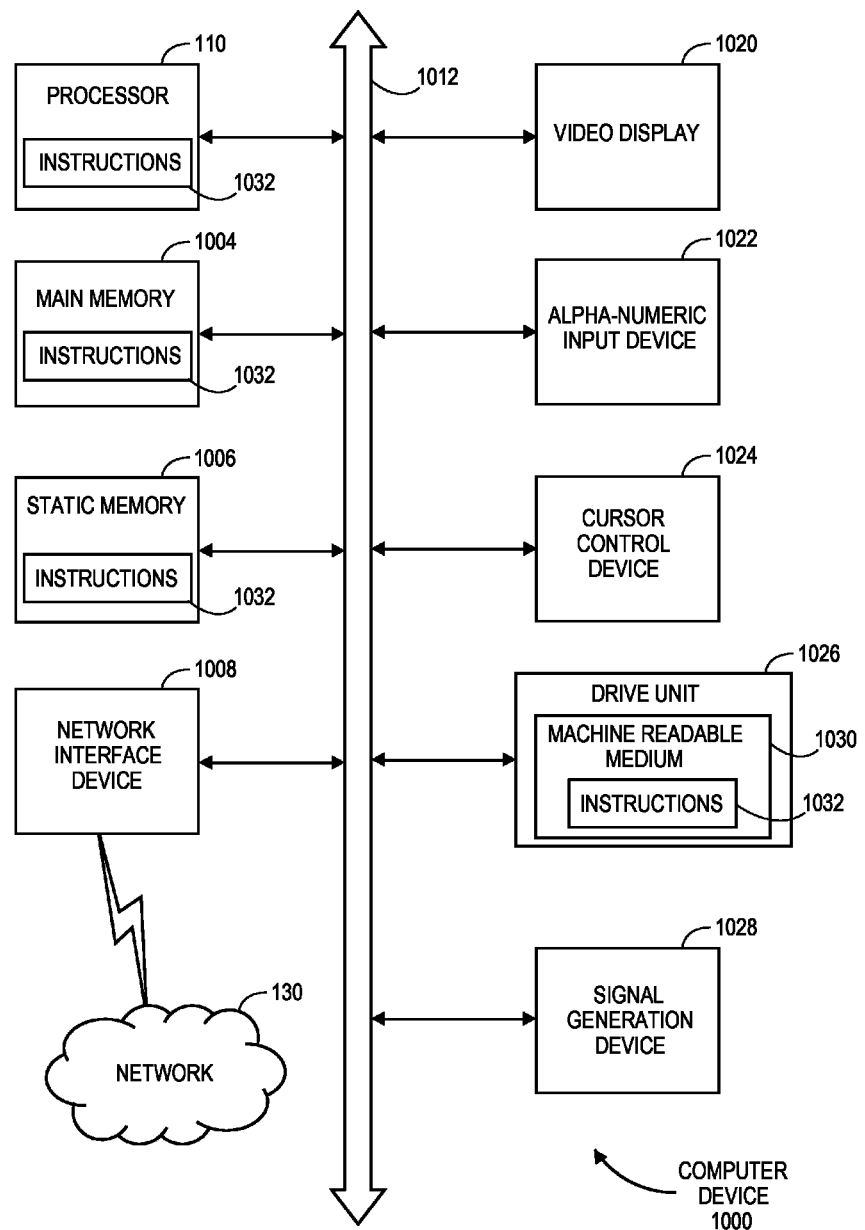
FIG. 10 shows a computer device 1000, in one embodiment.

FIG. 10 is a diagrammatic system view 1000 of a computer device view in which any of the embodiments disclosed herein may be performed, according to one embodiment. Particularly, the computer system view 1000 illustrates a processor 110, a main memory 1004, a static memory 1006, a bus 1012, a video display 1020, an alpha-numeric input device 1022, a cursor control device 1024, a drive unit 1026, a signal generation device 1028, a network interface device 1008, a machine readable medium 1030, instructions 1032, and a network 130, according to one embodiment.

Several examples are cited below for understanding the instant application for disease management system and mobile application. Several diseases categories: skin diseases, intensive care medicine, eye diseases, diseases diagnosed with non-invasive imaging such as but not limited to ultrasound and/or optical or photoacoustic imaging may be managed by this system.

As an example, but not limited to, a dermatological condition such as a mole or a rash may be bothering the user. They tap on the mobile application for disease management system and the screen prompts allows them to fill out the reason for contacting the services. Once they choose skin condition as an option or rash as an option they are prompted to take several system-directed pictures using the mobile device that image the condition as well as show the body part that is affected so that the location on the body may be documented. The user also enters key medical information and chooses a pharmacy. The user taps submit. The disease management system then algorithmically calculates all the necessary parameters such as location, local authority rules, HCP in the network; if not available then outside the network and sends the information about the user to the cloud database If the HCP is willing he indicates acceptance and the system provides them with the user/patient case. The HCP either chooses to further ask questions or provides diagnosis and treatment to the patient. As stated, machine learning involving algorithms for image processing provide a machine-suggested diagnosis and treatment for the HCP. The HCP can decline or accept the machine-created diagnosis and treatment suggestion. If the HCP requires more information he sends a message to the patient to provide specific information to help them. Once the HCP has provided the treatment, he may send the prescription to the nearest pharmacy or pharmacy of choice for the user. The system may also automatically do this if the HCP accepts the machine learning suggested diagnosis and treatment. The user then goes to the pharmacy and gets his medications. The HCP pay also provides an alternative treatment such as a massage or physiotherapy if the condition requires it. Suitable providers may also become network members to get referrals. The HCP may also offer an in-person appointment time if necessary. The entire communication is stored with the user specific records. Feedback provided by user about the HCP is used for ranking them as effective HCP to incentivize them to provide their valuable time for the disease management network.

As another example a 15 year old user has acne. The user uses a mobile device to login to access the disease management system. The first time the user accesses the system, the user creates an account. In this process, the user enters age, gender, medical history, medications, geographic location, and obtains parental consent if necessary. The user then selects a pharmacy, adds payment information, and/or insurance information, as well as any other pertinent data that would enable the physician to render the best diagnosis and treatment regimen. The user then takes photos of the areas of the skin affected by acne. The user may be trained in image acquisition by being walked through a simple instructional procedure for taking high quality images and/or videos. The patient may use touch screen technology to virtually draw or place a colored object on the image to capture an aspect of the disease. For example, the patient may represent different acne types such as white heads, black heads, and zits with white/red/black circles that the patient can place on the image and or body part within an image to demonstrate the areas that are affected. The patient then sends the information and images to a secure cloud and awaits a response from the physician. In this process, the patient may be presented with the option to select a physician based on geographic location and/or availability and/or cost and/or expertise and/or practice style and/or peer and/or customer review.

An HCP, in this case a physician, who wants to engage with patients using a mobile device will register with the disease management system. Verification of valid medical license will be performed. The physician will then create an account. In doing so, the physician will enter name, years of experience, practice expertise, geographic location, availability of time, price, interests, and practice style, and select other physicians that the physician knows to create a virtual practice. The physician then accesses the patient cases using the disease management system and a case is presented on the mobile device. The case may be first presented without personal health information and the physician can review the image quality prior to engaging in a true patient-physician relationship. If the image quality is not adequate, the physician can select to send a message relaying the need for better images. If the image is acceptable, the physician can select to take the case. At this point the physician can review all of the information submitted by the patient and review all of the images. The doctor then renders a diagnosis without or without the aid of the machine learning system. The disease management system or the doctor fills out the patient diagnosis and treatment regimen and if needed prescribes a medication directly to a pharmacy through the disease management system. The treatment recommendations may be depicted directly on the images that the patient submitted by animated and/or virtual drawings that demonstrate where the physician used touch screen technology to depict the topical treatment. Each treatment may be depicted with a different color. The physician and or machine create an invoice and submit it for reimbursement and/or the patient is charged at the time the user submits that case. The physician may follow-up with the patient. For example in the case of acne the physician prescribes oral doxycycline and topical clindamycin. The use of the topical application may be demonstrated by the physician using touch screen technology wherein the physician virtually draws on the patient images to demonstrate the areas for application of the topical medication. The physician can share the case with a colleague and refer the patient to another provider.

If a physician is using the machine learning platform. The images would be processed as mentioned above. The physician may benefit by the review and the answers provided by the image learning process.

The patient is alerted by the disease management system on a mobile device that the diagnosis and treatment are ready for review. The patient then accesses the diagnosis and treatment recommendations. The treatment recommendations may be depicted directly on the images that the patient submitted by animated and/or virtual drawings that demonstrate where the physician used touch screen technology to depict the topical treatment. Each treatment may be depicted with a different color. The physician and or machine create an invoice and submit it for reimbursement and/or the patient is charged at the time the user submits that case. The physician may follow-up with the patient.

Industrial application for the instant invention is many folds. The physicians and physicians in training may collect images during their practice and store them complying with HIPAA rules for furthering the study of medicine and contribute towards machine learning aided diagnosis process. The healthcare can be made affordable by connecting physicians to the price range elected by the user. The wait time for the user and the efficient time management by the physician help reduce the wait time. The new technology enables the data is created using cloud based technology and would be secured using HIPAA/HITECH compliant rules and made easily accessible by providers and users instantly. The application may be downloaded free or for a fee to a user's mobile device, healthcare provider's mobile device and linked to insurance provider, healthcare networks, pharmaceutical company and stores that provide prescription refills. The application may also have the capability to transform data to a fax or an email format if the recipient does not have the application on their device.

In addition, it will be appreciated that the various scenarios and methods of treatment disclosed herein may be embodied using means for achieving the various combinations of transaction and communication between user/patient and HCP treat a specific disease. Accordingly, the specification and drawings are to be regarded in an illustrative rather than a restrictive sense.

What is claimed is:
1. A method, comprising:
registering a user to use a data management system to obtain a treatment for a disease using an electronic mobile device;
uploading a user medical history to complete the registration by at least one of a self-filling form and prompt by offering predefined question and answer;
enabling the user to upload an image of a particular region of a user body wherein the user captures the image of the particular region of the user body using a camera connected to the electronic mobile device;
using a hardware processor, authenticating the uploaded image of the particular region of the user body for verification and authenticity by:
registering that a duplicate image of the particular region of the user body is taken and associating a first image, a second image and a third image for the same user;

processing the first image, second image and third image and converging as a third image or a combination of data to enhance the image quality and authenticate and verify the images for anatomical specificity and region prediction; and comparing the third image or the combination of data to a control image from a database, wherein the authentication also comprises checking for stock images and fraud prevention using a machine learning process;

recognizing a pattern for a differential diagnosis using a machine learning software running on machine readable medium, wherein the machine learning software uses input from a labeled image or an unlabeled image and compares that with a submitted image for predicting the disease; and storing a data generated by the user, medical history, forms, the image of the particular part of the body and the pattern for differential diagnosis in at least one of a local database and cloud server, wherein storing a data comprises securing the data using compliancy rules and storing the data in a compliant database.

2. The method of claim 1, wherein the verification also comprises comparing the images to an existing body of knowledge and database created by a physician and educational institution to perform suggestive differential diagnosis and provide a provisional diagnosis data.

3. The method of claim 2, further comprising:
enabling a physician to access the data generated by the user to provide a differential diagnosis;
viewing the provisional diagnosis data for the differential diagnosis;
rendering a diagnosis using at least one of the provisional diagnosis data, a physician diagnosis and a combination thereof; and
prescribing a treatment to the user based on the diagnosis.

4. The method of claim 3, further comprising:
receiving an alert regarding the physician's rendering of the treatment; and
obtaining at least one of a treatment method, a medication, a consultation date, a referral to another service provider and a combination thereof from the physician.

5. The method of claim 4, further comprising:
making an appointment for an in-person consultation date with a physician on a priority basis.

6. The method of claim 4, further comprising:
purchasing the medication using a proximity search, a best price search and a best mode search for obtaining the medication.

7. The method of claim 6, further comprising:
making a payment by using at least one of a personal money and insurance provider to the physician, drug store and an allied health professional.

8. The process of a disease management, comprising:
enabling a user to access medical care by using a mobile device having a processor;
uploading a user medical history, a file and a form as data to describe their disease for a physician to render a diagnosis and a treatment;
enabling the user to upload an image of a particular region of a user body wherein the user captures the image of the particular region of the user body using a camera connected to the electronic mobile device;
using a hardware processor, authenticating the uploaded image of the particular region of the user body for verification and authenticity by:

registering that a duplicate image of the particular region of the user body is taken and associating a first image, a second image and a third image for the same user;

processing the first image, second image and third image and converging as a final image or a combination of data to enhance the image quality and authenticate and verify the images for anatomical specificity and region prediction; and comparing the final image or the combination of data to a control image from a database, wherein the authentication also comprises checking for stock images and fraud prevention using a machine learning process;

recognizing a pattern for a differential diagnosis using a machine learning software running on machine readable medium, wherein the machine learning software uses input from a labeled image or an unlabeled image and compares that with a submitted image for predicting the disease; and storing a data generated by the user, medical history, forms, the image of the particular part of the body and the pattern for differential diagnosis in at least one of a local database and cloud server, wherein storing a data comprises securing the data using compliancy rules and storing the data in a compliant database.

9. The process of claim 8, further comprising:
uploading the image of the user for research, database creation and case study purposes in a compliant database by a student, researcher and a physician.

10. The process of claim 8, further comprising:
selecting a physician based on an expertise, availability, geographical proximity and affordability level; and
sending the data to the physician of selection.

11. The process of claim 8, further comprising:
receiving a data related to the user for a differential diagnosis and treatment; and
providing a diagnosis and the treatment for the user pertinent to the data.

12. The process of claim 11, wherein the data is a disease condition.

13. A system of disease management, comprising:
a mobile device comprising a processor, having a user registration module; and
a second device comprising a processor, having an image analysis module;
wherein the user registration module is configured to:
  register a user to use a data management system to obtain a disease treatment;
  upload a user medical history to complete the registration by at least one of a self-filling form and prompt by offering predefined question and answer;
  enable the user to upload an image of a particular region of a user body wherein the user captures the image of the particular region of the user body using a camera connected to the electronic mobile device;
wherein, using a hardware processor, the image analysis module is configured to:
  authenticate and verify the uploaded image of the particular region of the user body:
    registering that a duplicate image of the particular region of the user body is taken and associating a first image, a second image and a third image, wherein all images are of the same user;
    processing the first image, second image and third image and converging as a final image or a combination of data to enhance the image quality and authenticate and verify the image anatomical specificity and image region prediction; and comparing the final image or the combination of data to a control image from a database, wherein the authentication also comprises stock image and fraud prevention checking using a machine learning process;

recognize a differential diagnosis pattern using a machine learning software running on machine readable medium, wherein the machine learning software uses input from a labeled image or an unlabeled image and compares that with a submitted image to predict the disease; and store a data generated by the user, medical history, forms, the image of the particular part of the body and the differential diagnosis pattern in at least one of a local database and cloud server, wherein storing a data comprises securing the data using compliancy rules and storing the data in a compliant database.

14. The system of claim 13, further comprising:

a social media module to perform research on a disease condition, physician and treatment method by the user.

15. The system of claim 14, further comprising:

an audio video module to record the user input to generate data and the physician input to diagnose and treat.

16. The system of claim 14, further comprising:

a medical progress update module to monitor the advancement of the generated data, differential diagnosis, diagnosis and treatment.

17. The system of claim 14, further comprising:

a referral module to refer a specific case to a specific physician by the physician through the physician collaboration module.

18. The system of claim 17, further comprising:

a case storage module to collect images populated by the physician, user and a researcher.

* * * * *